(12) United States Patent
Kelleher

(10) Patent No.: US 10,974,063 B2
(45) Date of Patent: Apr. 13, 2021

(54) LIGHT THERAPY FOR EYELASH GROWTH

(71) Applicant: Tear Film Innovations, Inc.

(72) Inventor: Brian S. Kelleher, San Diego, CA (US)

(73) Assignee: Alcon Inc.

( * ) Notice: Subject to any disclaimer, the term of this patent is extended or adjusted under 35 U.S.C. 154(b) by 66 days.

(21) Appl. No.: 15/198,617

(22) Filed: Jun. 30, 2016

(65) Prior Publication Data

US 2018/0001108 A1    Jan. 4, 2018

(51) Int. Cl.
*A61N 5/06* (2006.01)
*A61F 9/007* (2006.01)
*A61N 5/067* (2006.01)

(52) U.S. Cl.
CPC .......... *A61N 5/0617* (2013.01); *A61F 9/0079* (2013.01); *A61F 9/00772* (2013.01); *A61N 5/0624* (2013.01); *A61N 2005/067* (2013.01); *A61N 2005/0644* (2013.01); *A61N 2005/0651* (2013.01); *A61N 2005/0654* (2013.01); *A61N 2005/0659* (2013.01); *A61N 2005/0662* (2013.01)

(58) Field of Classification Search
CPC .......... A61N 5/0617; A61N 2005/0644; A61N 5/0624
See application file for complete search history.

(56) References Cited

U.S. PATENT DOCUMENTS

| | | |
|---|---|---|
| 793,004 A | 6/1905 | May |
| 1,006,945 A | 10/1911 | Houston |
| 1,714,693 A | 5/1929 | Renwick |
| 1,924,315 A | 8/1933 | Hemphill et al. |
| 1,963,990 A | 6/1934 | Gilkeson et al. |
| 2,183,726 A | 12/1939 | Sommer et al. |
| 2,204,631 A | 6/1940 | Tillyer |
| 2,231,112 A | 2/1941 | Conner |
| 2,407,518 A | 9/1946 | Schauweker |

(Continued)

FOREIGN PATENT DOCUMENTS

| | | |
|---|---|---|
| CA | 2679448 A1 | 9/2008 |
| CN | 2400107 Y | 10/2000 |

(Continued)

OTHER PUBLICATIONS

Kent, Christopher. "Intense Pulsed Light: for Treating Dry Eye." *Review of Ophthalmology.* Nov. 16, 2010. 4 pages.

(Continued)

*Primary Examiner* — Eric D. Bertram

(57) ABSTRACT

Systems, methods, and devices for promoting eyelash hair growth includes an energy transducer, positionable proximate the eyelid, configured to provide light energy to a user's eyelids at an output wavelength suitable for stimulating eyelash hair growth, and a scleral shield, positionable inside of the eyelid, to protect the eye from the light energy. The device may be powered by an internal power source, such as a rechargeable battery or disposable batteries, or by an external power source, such as a plug used in connection with an AC outlet. In use, the eyelid is positioned between the energy transducer and the scleral shield, and the light energy from the energy transducer is applied to the eyelash region of the eyelid to promote eyelash hair growth.

4 Claims, 5 Drawing Sheets

(56) References Cited

U.S. PATENT DOCUMENTS

| | | |
|---|---|---|
| 2,545,724 A | 3/1951 | Curtis |
| 2,555,636 A | 6/1951 | Felts et al. |
| 2,690,173 A | 9/1954 | Seeger et al. |
| 2,891,252 A | 6/1959 | Lazo |
| 3,140,390 A | 7/1964 | Smith et al. |
| 3,173,419 A | 3/1965 | Dubilier et al. |
| 3,333,586 A | 8/1967 | Bellis et al. |
| 3,404,678 A | 10/1968 | Von Ardenne |
| 3,411,364 A | 11/1968 | Horley et al. |
| 3,485,244 A | 12/1969 | Rosen |
| 3,667,476 A | 6/1972 | Muller |
| 3,934,585 A | 1/1976 | Maurice |
| 3,952,735 A | 4/1976 | Wirtschafter et al. |
| RE28,873 E | 6/1976 | Morgan |
| 4,167,942 A | 9/1979 | Brunelli |
| 4,261,364 A | 4/1981 | Haddad et al. |
| 4,303,063 A | 12/1981 | Stahl |
| 4,387,707 A | 6/1983 | Polikoff |
| 4,398,811 A | 8/1983 | Nishioka et al. |
| 4,549,051 A | 10/1985 | Ness |
| 4,554,911 A | 11/1985 | Nielsen |
| 4,570,626 A | 2/1986 | Norris et al. |
| 4,669,834 A | 6/1987 | Richter |
| 4,736,743 A | 4/1988 | Daikuzono |
| 4,778,457 A | 10/1988 | York |
| 4,784,165 A | 11/1988 | Stein |
| 4,824,730 A | 4/1989 | Fukuda et al. |
| 4,883,454 A | 11/1989 | Hamburg |
| 4,914,088 A | 4/1990 | Glonek et al. |
| 4,955,377 A | 9/1990 | Lennox et al. |
| 4,958,632 A | 9/1990 | Duggan |
| 5,030,214 A | 7/1991 | Spector |
| 5,097,829 A | 3/1992 | Quisenberry |
| 5,151,100 A | 9/1992 | Abele et al. |
| 5,158,082 A | 10/1992 | Jones |
| 5,169,384 A | 12/1992 | Bosniak et al. |
| 5,213,097 A | 5/1993 | Zeindler |
| 5,224,469 A | 7/1993 | Mocny |
| 5,251,025 A | 10/1993 | Cooper et al. |
| 5,251,627 A | 10/1993 | Morris |
| 5,283,063 A | 2/1994 | Freeman |
| 5,314,456 A | 5/1994 | Cohen |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,377,701 A | 1/1995 | Fang |
| 5,417,686 A | 5/1995 | Peterson et al. |
| 5,425,380 A | 6/1995 | Hudson et al. |
| 5,484,432 A | 1/1996 | Sand |
| 5,496,311 A | 3/1996 | Abele et al. |
| 5,601,548 A | 2/1997 | Smith et al. |
| 5,627,611 A | 5/1997 | Scheiner |
| 5,628,772 A | 5/1997 | Russell |
| 5,643,336 A | 7/1997 | Lopez-Claros |
| 5,690,608 A | 11/1997 | Watanabe et al. |
| 5,700,238 A | 12/1997 | Hyson |
| 5,720,773 A | 2/1998 | Lopez-Claros |
| 5,769,806 A | 6/1998 | Radow |
| 5,807,357 A | 9/1998 | Kang |
| 5,836,927 A | 11/1998 | Fried |
| 5,893,719 A | 4/1999 | Radow |
| 5,958,912 A | 9/1999 | Sullivan |
| 5,964,723 A | 10/1999 | Augustine |
| 6,024,095 A | 2/2000 | Stanley, III |
| 6,058,324 A | 5/2000 | Chance |
| 6,059,772 A | 5/2000 | Hsia et al. |
| 6,098,628 A | 8/2000 | Funk |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,123,081 A | 9/2000 | Durette |
| 6,153,607 A | 11/2000 | Pflugfelder et al. |
| 6,155,995 A | 12/2000 | Lin |
| 6,161,546 A | 12/2000 | Yavitz |
| 6,181,970 B1 | 1/2001 | Kasevich |
| 6,193,740 B1 | 2/2001 | Rodriguez |
| 6,201,880 B1 | 3/2001 | Elbaum et al. |
| 6,206,842 B1 | 3/2001 | Tu et al. |
| 6,213,966 B1 | 4/2001 | Augustine |
| 6,273,886 B1 | 8/2001 | Edwards et al. |
| 6,309,364 B1 | 10/2001 | Cathaud et al. |
| D456,079 S | 4/2002 | Fujii |
| 6,423,018 B1 | 7/2002 | Augustine |
| 6,425,888 B1 | 7/2002 | Embleton et al. |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,257 B2 | 4/2003 | Nagase et al. |
| D477,084 S | 7/2003 | Menezes et al. |
| 6,641,264 B1 | 11/2003 | Schwebel |
| 6,648,904 B2 | 11/2003 | Altshuler et al. |
| 6,706,001 B2 | 3/2004 | Fresco |
| 6,743,249 B1 | 6/2004 | Alden |
| 6,780,176 B2 | 8/2004 | Hasegawa |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,897,238 B2 | 5/2005 | Anderson |
| 6,908,195 B2 | 6/2005 | Fuller |
| 6,925,317 B1 | 8/2005 | Samuels et al. |
| 6,974,454 B2 | 12/2005 | Hooven |
| 6,979,328 B2 | 12/2005 | Baerveldt et al. |
| 6,989,007 B2 | 1/2006 | Shadduck |
| 7,001,379 B2 | 2/2006 | Behl et al. |
| 7,004,942 B2 | 2/2006 | Laird et al. |
| 7,036,928 B2 | 5/2006 | Schwebel |
| 7,069,084 B2 | 6/2006 | Yee |
| 7,108,694 B2 | 9/2006 | Miura et al. |
| 7,118,217 B2 | 10/2006 | Kardon et al. |
| 7,118,591 B2 | 10/2006 | Frank et al. |
| 7,121,666 B2 | 10/2006 | Tseng et al. |
| 7,122,013 B2 | 10/2006 | Liu |
| 7,122,047 B2 | 10/2006 | Grahn et al. |
| 7,123,968 B1 | 10/2006 | Casscells, III et al. |
| 7,184,827 B1 | 2/2007 | Edwards |
| 7,211,070 B2 | 5/2007 | Soroudi |
| 7,229,468 B2 | 6/2007 | Wong, Jr. et al. |
| 7,231,922 B2 | 6/2007 | Davison et al. |
| D546,459 S | 7/2007 | Banryu |
| D552,736 S | 10/2007 | Yamaoka |
| D553,750 S | 10/2007 | Yamaoka |
| 7,316,657 B2 | 1/2008 | Kleinhenz et al. |
| 7,357,500 B2 | 4/2008 | Schwebel |
| 7,435,252 B2 | 10/2008 | Krespi et al. |
| 7,442,174 B2 | 10/2008 | Butler |
| 7,513,893 B2 | 4/2009 | Soroudi |
| 7,594,728 B2 | 9/2009 | Seal et al. |
| D612,941 S | 3/2010 | Youngquist et al. |
| D614,774 S | 4/2010 | Gausmann et al. |
| 7,712,899 B2 | 5/2010 | Tanassi et al. |
| 7,771,342 B2 | 8/2010 | Rademacher et al. |
| 7,811,252 B2 | 10/2010 | Dacquay et al. |
| 7,886,748 B2 | 2/2011 | Boxer Wachler |
| 7,976,573 B2 | 7/2011 | Korb et al. |
| 7,981,146 B2 | 7/2011 | Korb et al. |
| 7,981,147 B2 | 7/2011 | Korb et al. |
| 8,007,424 B2 | 8/2011 | Moser et al. |
| 8,025,689 B2 | 9/2011 | Korb et al. |
| 8,083,787 B2 | 12/2011 | Korb et al. |
| 8,187,310 B2 | 5/2012 | Korb et al. |
| 8,187,311 B2 | 5/2012 | Korb et al. |
| 8,202,853 B2 | 6/2012 | Adkins, Jr. |
| 8,235,887 B2 | 8/2012 | Bayer et al. |
| 8,249,695 B2 | 8/2012 | Grenon et al. |
| 8,255,039 B2 | 8/2012 | Gravely et al. |

(56) References Cited

U.S. PATENT DOCUMENTS

| | | |
|---|---|---|
| 8,348,955 B2 | 1/2013 | Truckai et al. |
| 8,409,848 B2 | 4/2013 | Zeng et al. |
| 8,491,505 B2 | 7/2013 | Yang |
| 8,491,508 B2 | 7/2013 | Smith et al. |
| 8,506,539 B2 | 8/2013 | Guinan et al. |
| 8,523,928 B2 | 9/2013 | Korb et al. |
| 8,562,658 B2 | 10/2013 | Shoham |
| 8,600,484 B2 | 12/2013 | Grenon et al. |
| 8,617,229 B2 | 12/2013 | Korb et al. |
| 8,628,504 B2 | 1/2014 | Grenon et al. |
| 8,632,578 B2 | 1/2014 | Korb et al. |
| 8,685,073 B2 | 4/2014 | Korb et al. |
| 9,060,843 B2 | 6/2015 | Grenon et al. |
| 2001/0039442 A1 | 11/2001 | Gorge et al. |
| 2001/0041886 A1 | 11/2001 | Durkin et al. |
| 2002/0035345 A1 | 3/2002 | Beck |
| 2002/0099094 A1 | 7/2002 | Anderson |
| 2002/0111608 A1 | 8/2002 | Baerveldt et al. |
| 2002/0128696 A1 | 9/2002 | Pearl et al. |
| 2002/0180929 A1 | 12/2002 | Tseng et al. |
| 2003/0056281 A1 | 3/2003 | Hasegawa |
| 2003/0065277 A1 | 4/2003 | Covington |
| 2003/0069489 A1 | 4/2003 | Abreu |
| 2003/0100936 A1 | 5/2003 | Altshuler et al. |
| 2003/0114426 A1 | 6/2003 | Pflugfelder et al. |
| 2003/0139790 A1 | 7/2003 | Ingle et al. |
| 2003/0195438 A1 | 10/2003 | Petillo |
| 2003/0211043 A1 | 11/2003 | Korb |
| 2003/0233135 A1 | 12/2003 | Yee |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0111138 A1 | 6/2004 | Bleam et al. |
| 2004/0153093 A1 | 8/2004 | Donovan |
| 2004/0167499 A1 | 8/2004 | Grove et al. |
| 2004/0186534 A1 | 9/2004 | Shadduck |
| 2004/0199158 A1 | 10/2004 | Hood et al. |
| 2004/0237969 A1 | 12/2004 | Fuller |
| 2004/0249427 A1 | 12/2004 | Nabilsi |
| 2004/0260209 A1 | 12/2004 | Ella et al. |
| 2005/0022823 A1 | 2/2005 | Davison et al. |
| 2005/0119629 A1 | 6/2005 | Soroudi |
| 2005/0143798 A1 | 6/2005 | Bleam et al. |
| 2005/0177093 A1 | 8/2005 | Barry et al. |
| 2005/0220742 A1 | 10/2005 | Breen |
| 2005/0234506 A1 | 10/2005 | Weser |
| 2006/0018953 A1 | 1/2006 | Guillon et al. |
| 2006/0030604 A1 | 2/2006 | Elsinger et al. |
| 2006/0030908 A1 | 2/2006 | Powell et al. |
| 2006/0055878 A1 | 3/2006 | Yee |
| 2006/0069420 A1 | 3/2006 | Rademacher et al. |
| 2006/0104914 A1 | 5/2006 | Soroudi |
| 2006/0135890 A1 | 6/2006 | Tsai |
| 2006/0136022 A1 | 6/2006 | Wong et al. |
| 2006/0139569 A1 | 6/2006 | Schwebel |
| 2006/0154901 A1 | 7/2006 | Pflugfelder et al. |
| 2006/0157064 A1 | 7/2006 | Davison et al. |
| 2006/0183698 A1 | 8/2006 | Abelson |
| 2006/0223032 A1 | 10/2006 | Fried et al. |
| 2006/0233859 A1 | 10/2006 | Whitcup et al. |
| 2007/0016254 A1 | 1/2007 | Grenon et al. |
| 2007/0016256 A1 | 1/2007 | Korb et al. |
| 2007/0027411 A1 | 2/2007 | Ella et al. |
| 2007/0049913 A1 | 3/2007 | Grenon et al. |
| 2007/0088415 A1 | 4/2007 | Peyman |
| 2007/0173799 A1 | 7/2007 | Hsia |
| 2007/0191821 A1 | 8/2007 | Boxer Wachler |
| 2007/0203462 A1 | 8/2007 | Soroudi |
| 2007/0270760 A1 | 11/2007 | Dacquay et al. |
| 2007/0280924 A1 | 12/2007 | Daniels et al. |
| 2007/0282282 A1 | 12/2007 | Wong et al. |
| 2008/0051741 A1 | 2/2008 | Grenon et al. |
| 2008/0075787 A1 | 3/2008 | Hibino |
| 2008/0081999 A1 | 4/2008 | Gravely et al. |
| 2008/0082057 A1 | 4/2008 | Korb et al. |
| 2008/0109053 A1 | 5/2008 | Grenon et al. |
| 2008/0114423 A1 | 5/2008 | Grenon et al. |
| 2008/0114425 A1 | 5/2008 | Korb et al. |
| 2008/0114427 A1 | 5/2008 | Korb et al. |
| 2008/0132973 A1 | 6/2008 | Lord et al. |
| 2008/0132978 A1 | 6/2008 | Korb et al. |
| 2008/0275533 A1 | 11/2008 | Powell |
| 2009/0043365 A1 | 2/2009 | Friedland et al. |
| 2009/0137533 A1 | 5/2009 | Adkins, Jr. |
| 2009/0306111 A1 | 12/2009 | Nakamura et al. |
| 2010/0100029 A1 | 4/2010 | Maskin |
| 2010/0121420 A1 | 5/2010 | Fiset et al. |
| 2010/0152645 A1 | 6/2010 | Ogasawara |
| 2010/0152719 A1 | 6/2010 | Fujikawa |
| 2010/0292630 A1 | 11/2010 | Maskin |
| 2011/0022010 A1 | 1/2011 | Grenon et al. |
| 2011/0039805 A1 | 2/2011 | Pflugfelder et al. |
| 2011/0059902 A1 | 3/2011 | Sullivan et al. |
| 2011/0059925 A1 | 3/2011 | Donnenfeld |
| 2011/0130729 A1 | 6/2011 | Korb et al. |
| 2011/0196353 A1* | 8/2011 | DeLand .............. A61N 5/0616 606/9 |
| 2011/0251532 A1 | 10/2011 | Yang |
| 2011/0273550 A1 | 11/2011 | Amano et al. |
| 2011/0319794 A1 | 12/2011 | Gertner |
| 2012/0016450 A1 | 1/2012 | Korb et al. |
| 2012/0065556 A1 | 3/2012 | Smith et al. |
| 2012/0088980 A1 | 4/2012 | Gravely et al. |
| 2012/0109041 A1 | 5/2012 | Munz |
| 2012/0136285 A1 | 5/2012 | Korb et al. |
| 2012/0209154 A1 | 8/2012 | Williams, III et al. |
| 2012/0215073 A1 | 8/2012 | Sherman et al. |
| 2012/0221081 A1 | 8/2012 | Hof et al. |
| 2013/0053733 A1 | 2/2013 | Korb et al. |
| 2013/0110101 A1 | 5/2013 | Van Valen et al. |
| 2013/0172829 A1 | 7/2013 | Badawi |
| 2013/0172959 A1 | 7/2013 | Azoulay |
| 2014/0330129 A1 | 11/2014 | Grenon et al. |
| 2015/0005750 A1* | 1/2015 | Kelleher ................ A61N 7/00 606/3 |
| 2015/0025545 A1 | 1/2015 | Grenon et al. |
| 2015/0057701 A1* | 2/2015 | Kelleher ............ A61F 9/00718 606/204.15 |
| 2015/0100063 A1 | 4/2015 | Korb et al. |
| 2016/0106576 A1 | 4/2016 | Badawi et al. |
| 2018/0092773 A1 | 4/2018 | Kelleher et al. |
| 2019/0091065 A1 | 3/2019 | Kelleher et al. |

FOREIGN PATENT DOCUMENTS

| | | |
|---|---|---|
| DE | 19645432 A1 | 5/1998 |
| DE | 202005011496 U1 | 7/2006 |
| EP | 1587468 B1 | 1/2011 |
| EP | 2151438 B1 | 10/2012 |
| JP | H7-28523 U | 5/1995 |
| JP | H1085248 A | 4/1998 |
| JP | 2004236727 A | 8/2004 |
| JP | 2006198249 A | 8/2006 |
| JP | 2008-540051 A | 11/2008 |
| JP | 2010-516343 A | 5/2010 |
| JP | 2010155012 A | 7/2010 |
| WO | WO-99/09920 A1 | 3/1999 |
| WO | WO-99/09965 A2 | 3/1999 |
| WO | WO-99/20213 A1 | 4/1999 |
| WO | WO-99/58131 A1 | 11/1999 |
| WO | WO-02/05743 A1 | 1/2002 |
| WO | WO-02/056781 A1 | 7/2002 |
| WO | WO-03/061535 A2 | 7/2003 |
| WO | WO-03/072008 A2 | 9/2003 |
| WO | WO-2004/041134 A1 | 5/2004 |
| WO | WO-2006/058189 A2 | 6/2006 |
| WO | WO-2006/093851 A2 | 9/2006 |
| WO | WO-2006/125106 A1 | 11/2006 |
| WO | WO-2008/024100 A2 | 2/2008 |
| WO | WO-2008/072169 A2 | 6/2008 |
| WO | WO-2008/089327 A1 | 7/2008 |
| WO | WO-2008/106228 A2 | 9/2008 |
| WO | WO-2009/064834 A2 | 5/2009 |

(56) References Cited

FOREIGN PATENT DOCUMENTS

| WO | WO-2010/005527 A1 | 1/2010 |
| WO | WO-2010/056848 A1 | 5/2010 |
| WO | WO-2011/067941 A1 | 6/2011 |

OTHER PUBLICATIONS

Outram, Bernie. "Black Coatings to Reduce Stray Light." *OPTI 521—Optomechanical Engineering*. Fall 2009. 13 pages.

Ayliffe, William. "Blepharitis and Meibomian Gland Dysfunction." *Smolin and Thoft's The Cornea: Scientific Foundations & Clinical Practice*. Ed. C. S. Foster. 4th ed. 2005. 649-50.

Bickerton, Reginald E. "Notes on Ophthalmology in Vienna." *The British Medical Journal* (1898): 818-21.

Connor, Leartus, *Hot Water in the Management of Eye Diseases. Some Suggestions*. Detroit: D.O. Haynes, (1887). 18 pages.

Fein, W. "Cautery Applications to Relieve Punctal Stenosis." *Archives of Ophthalmology* 95.1 (1977): 145-46.

Friedland, Beth R., Christopher P. Fleming, Caroline A. Blackie, and Donald R. Korb. "A Novel Thermodynamic Treatment for Meibomian Gland Dysfunction." *Current Eye Research* 36.2 (2011): 79-87. Print.

Goto, E. "Treatment of Non-inflamed Obstructive Meibomian Gland Dysfunction by an Infrared Warm Compression Device." *British Journal of Ophthalmology* 86.12 (2002): 1403-407.

Gutgesell, Vicki J., George A. Stern, and C. Ian Hood. "Histopathology of Meibomian Gland Dysfunction." *American Journal of Ophthalmology* 94.3 (1982): 383-87.

Henriquez, A. S., and D. R. Korb. "Meibomian Glands and Contact Lens Wear." *British Journal of Ophthalmology* 65.2 (1981): 108-11.

Jester, J. V. et al. "Meibomian Gland Dysfunction." *Investigative Ophthalmology & Visual Science* 30 (1989): 927-51.

Korb, D. R., and A. S. Henriquez. "Meibomian Gland Dysfunction and Contact Lens Intolerance." *J. Amer Optometric Assoc*. 51.3 (1980): 243-51.

Korb, Donald R., and Jack V. Greiner. "Increase in Tear Film Lipid Layer Thickness Following Treatment of Meibomian Gland Dysfunction." *Advances in Experimental Medicine and Biology Lacrimal Gland, Tear Film, and Dry Eye Syndromes* (1994): 293-98.

Minco. *Flexible Heaters Design Guide*. (2007). 64 pages.

Mori, A. "Disposable Eyelid-warming Device for the Treatment of Meibomian Gland Dysfunction." *Japanese Journal of Ophthalmology* 47.6 (2003): 578-86.

Mori, Asako, Yoshihisa Oguchi, Eiki Goto, Katsu Nakamori, Tomohiro Ohtsuki, Fuminobu Egami, Jun Shimazaki, and Kazuo Tsubota. "Efficacy and Safety of Infrared Warming of the Eyelids." *Cornea* 18.2 (1999): 188.

Wise, Ryan J., Rachel K. Sobel, and Richard C. Allen. "Meibography: A Review of Techniques and Technologies." *Saudi Journal of Ophthalmology* 26.4 (2012): 349-56.

Yokoi, Norihiko. "Assessment of Meibomian Gland Function in Dry Eye Using Meibometry." *Archives of Ophthalmology Arch Ophthalmol* 117.6 (1999): 723-29.

* cited by examiner

LIGHT THERAPY FOR EYELASH GROWTH

CROSS-REFERENCE TO RELATED APPLICATIONS

This application is a continuation-in-part of U.S. patent application Ser. No. 14/265,228 filed Apr. 29, 2014 and entitled "Systems and Methods for the Treatment of Eye Conditions", which claims the benefit of U.S. Provisional Application No. 61/817,757, filed Apr. 30, 2013, which are incorporated herein by reference, and related to U.S. patent application Ser. No. 14/529,102 and entitled "Systems and Methods for the Treatment of Eye Conditions", which is also incorporated herein by reference.

BACKGROUND

The present disclosure relates to medical devices and methods of using the same. More particularly, the disclosure relates to systems, methods, and apparatus used to treat eyelashes and surrounding tissue.

Eyelashes grow at the edge of the eyelid and help filter out foreign matter, including dust and debris, and prevent the foreign matter from getting into the eye. An eyelash is sensitive to being touched, thus providing a warning that an object may be too close to the eye. Many people lose their eyelashes, a condition called madarosis. There are numerous conditions that can result in eyelash loss, including ophthalmological conditions, such as blepharitis, dermatologic conditions, Nutritional defects, Infections, Trauma, Drugs/Medications, Genetics, and other diseases.

A blepharitis attack of eyelids repeatedly can cause eyelash loss. It causes swelling and itching on the eyelid due to excessive bacteria growth in tiny oil glands. Antibiotics are typically used to combat the bacterial infection. Blepharitis can include anterior blepharitis or posterior blepharitis. Anterior blepharitis is usually either staphylococcal or seborrhoeic, and posterior blepharitis refers to any of the varieties of meibomian gland dysfunction. The symptoms of anterior blepharitis include itching, burning, foreign body sensation, photophobia, and tearing. Posterior blepharitis is also known as meibomian gland dysfunction and is characterized by either excessive foam in the tear film in the hypersecretory type, or plugging of the meibomian orifices in the obstructive type. Expression of the secretions reveals a turbid or toothpaste-like material. If there is spillover inflammation of the anterior lid margin, there may be a loss of eyelashes.

A need exists for improved methods and devices to diagnose and treat eyelash loss.

SUMMARY

Embodiments described herein may meet one or more of the needs identified above and may overcome one or more of the shortcomings of current eyelash treatment methods. Various implementations of systems, methods, and devices within the scope of the appended claims each have several aspects, no single one of which is solely responsible for the desirable attributes described herein. Without limiting the scope of the appended claims, some prominent features are described herein.

The present application relates generally to treatment systems, methods, and devices used to treat eyelids, in particular, the eyelid margin where the eyelashes grow. Details of one or more implementations of the subject matter described in this specification are set forth in the accompanying drawings and the description below. Other features, embodiments, and advantages will become apparent from the description, the drawings, and the claims.

One aspect of this disclosure provides a device for stimulating and/or promoting eyelash growth. In various embodiments, the device includes an energy transducer configured to provide light energy at one or more wavelengths and a scleral shield. When the eyelid is positioned between the energy transducer and the scleral shield, the light energy from the energy transducer is directed to the eyelid margin to provide light energy at an output wavelength suitable for stimulating and/or promote eyelash hair growth.

An additional aspect of the disclosure provides a method for promoting eyelash growth. The method includes positioning an energy transducer proximate an eyelash region of the eyelid, the energy transducer configured to provide light energy at one or more wavelengths, and positioning a scleral shield between the energy transducer and eyeball, the scleral shield being made of, or coated with, a light energy blocking material. The method also includes directing light energy from the energy transducer toward the eyelash region at a first wavelength suitable for stimulating and/or promoting eyelash hair growth; and blocking any light energy directed toward the eyeball with the scleral shield to protect the eyeball from the light energy.

In some embodiments, the energy transducer is further configured to provide light energy at a second wavelength selected to treat bacteria. In some embodiments, the energy transducer is further configured to provide light energy at a third wavelength selected to be absorbed by the eyelid tissue, and thereby heat the eyelid tissue. The first wavelength may be in the range of about (without limitation) 450-700 nm, the second wavelength may be in the range of about (without limitation) 400-450 nm and the third wavelength may be in the range of about (without limitation) 700-1000 nm.

In some embodiments, the energy transducer may include at least one of an LED, laser, incandescent lamp, xenon lamp, halogen lamp, luminescent lamp, high-intensity discharge lamp, and gas discharge lamp.

Some embodiments of the device further include one or more components selected from the group consisting of: a display or dashboard configured to display the device status; a battery configured to power the device components; battery charging means; a controller; printed circuit board; and communication circuitry between scleral shield and energy transducer.

Some embodiments of the device further include a safety feature electrically coupled to the energy transducer configured to prevent or interrupt the light energy from the energy transducer if the if the scleral shield and associated assembly are not properly attached to, and aligned with, the device.

Additionally, or alternatively, some embodiments of the device further include a timer operatively coupled to the energy transducer and configured to shut off the energy transducer after a predetermined time.

Other features and advantages should be apparent from the following description of various implementations, which illustrate, by way of example, the principles of the invention.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

DETAILED DESCRIPTION

Figure 1:
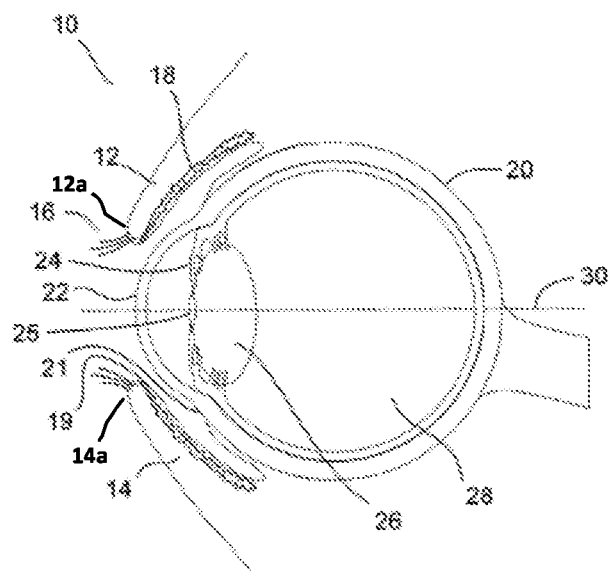
FIG. 1 is a cross-sectional diagram of a mammalian eye system 10.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "have," "having," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational and directional terms are used. "Connected" and "coupled," and variations thereof, as used herein include direct connections, such as being contiguously formed with, or glued, or otherwise attached directly to, on, within, etc. another element, as well as indirect connections where one or more elements are disposed between the connected elements. "Connected" and "coupled" may refer to a permanent or non-permanent (i.e., removable) connection.

"Secured" and variations thereof as used herein include methods by which an element is directly secured to another element, such as being glued, screwed, or otherwise fastened directly to, on, within, etc. another element, as well as indirect means of securing two elements together where one or more elements are disposed between the secured elements.

"Proximal" and "distal" are relational terms used herein to describe position from the perspective of a medical professional treating a patient. For example, as compared to "distal," the term "proximal" refers to a position that is located more closely to the medical professional, while the distal end is located more closely to the patient during treatment. For example, the distal ends of the devices disclosed herein oppose the proximal ends of the same devices, and the distal end of a device often includes, for example, the end configured for placement against the eyelid of a patient.

"Transducer" is a term used herein to describe an element which receives one form of energy and transforms it into another. For example, a light source may receive electrical energy and produce light energy. Likewise, an ultrasonic transducer may receive electrical energy and produce ultrasonic energy.

"Light" as used herein refers not only to energy in the visible light spectrum, but also to energy in the infrared and ultraviolet portions of the electromagnetic energy spectrum.

"Waveguide" as used herein refers to any means of influencing the propagation, distribution or trajectory of electromagnetic energy such as light, ultrasonic energy and radio frequency energy. As defined herein, optical elements such as diffractors, refractors, diffusers and the like are included in this broad definition of a waveguide.

"Optical path length" is used herein to describe the length of the path (for example, within a tissue section) through which energy travels.

Embodiments disclosed herein relate to ophthalmic devices, systems, and methods. The devices, systems, and methods disclosed herein can be used to for stimulating and/or promoting eyelash growth. FIG. 1 is a cross-sectional diagram of a mammalian eye system 10, which includes an eyeball 20 and surrounding eyelid anatomy. As recited within this disclosure and as identified in FIG. 1, the "central ocular axis" 30 of the eye is the central axis running through the center of the cornea 22, iris 24, pupil 25, lens 26, and vitreous body 28 of the eyeball 20. Eye system 10 includes an upper eyelid 12, a lower eyelid 14, and eyelashes 16. Within the tissue of each eyelid 12, 14, there are meibomian glands 18 each having a duct or orifice 19. In healthy eye systems 10, the meibomian glands 18 secrete out of ducts 19 a substance called meibum, comprised primarily of lipids and proteins. The meibum forms part of the tear film that covers the surface of the eyeball 20.

Figure 2A:
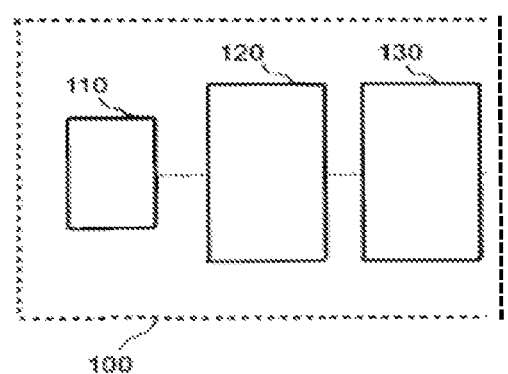
FIG. 2A is a schematic block diagram of one embodiment of an eyelash treatment device according to some embodiments.

FIG. 2A is a schematic block diagram of an example eyelash treatment device 100 according to various embodiments. As shown in FIG. 2A, the depicted device 100 includes a power source module 110, an energy transducer module 120, and an optional energy waveguide module 130, which may be functionally and/or physically connected to one another. In some embodiments, the energy transducer module 120 and energy waveguide module 130 may be combined in a single unit, such as within a single housing for example.

The power source module 110 of various embodiments provides energy to the energy transducer module 120. The power source module 110 may include any structure configured for delivering power to one or more other components of the eyelash treatment device 100. In some embodiments, the power source module 110 includes a disposable battery, a rechargeable battery, a solar cell, a power transforming module such as a power supply or power converter, or a power transfer mechanism such as a cord, outlet, or plug configured to receive alternating current or direct current from an external source.

The energy transducer module 120 may include one or more energy transducers configured to emit one or more forms or type of energy. For example, as described in more detail below, in some embodiments, the energy transducers emit photonic, acoustic, radio frequency, electrical, magnetic, electro-magnetic, vibrational, infrared or ultrasonic energy. In some embodiments, the transducer module 120 generates multiple types of energy simultaneously or in a predetermined order.

Figure 2B:
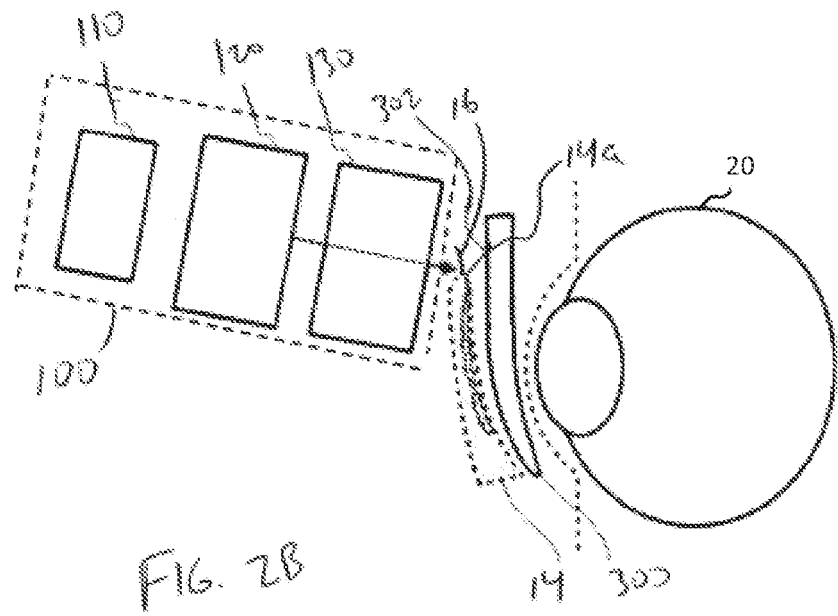
FIG. 2B is a schematic block diagram of another embodiment of an eyelash treatment device having a scleral shield.
Figure 2C:
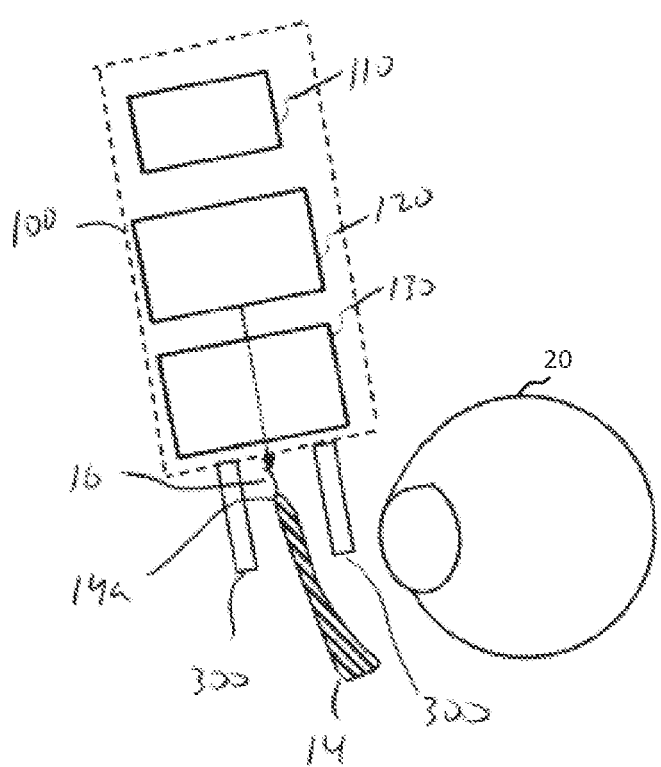
FIG. 2C is a schematic block diagram of another embodiment of an eyelash treatment device having attached scleral shields.

FIGS. 2B and 2C show the eyelash treatment device 100 with optional energy waveguide module 130 that includes one or more structures configured to control or focus the direction of energy emission from the energy transducers and a scleral shield 300 made of light energy blocking material or have a light energy blocking surface on a front face 302 to block light energy from entering the eyeball during treatment. The waveguide module 130 may include one or more reflectors, refractors, diffractors, or diffusers (described in more detail below) configured to focus photonic energy toward a desired region, or other structures for configuring and directing the energy emission, such as ultrasonic horns or fiber optics.

In some embodiments, the transducer module 120 may generate multiple types of energy simultaneously, such as photonic, acoustic, radio frequency, electrical, magnetic, electro-magnetic, vibrational, infrared or ultrasonic energy. For example, a first energy may treat the eyelash at the eyelid margin while a second energy may treat for bacteria on the eyelid.

The embodiment shown in FIG. 2C is similar to the embodiment shown in FIG. 2B except there are two scleral shields 300. The eyelid is placed within the scleral shields 300 during eyelash treatment.

Figure 3A:
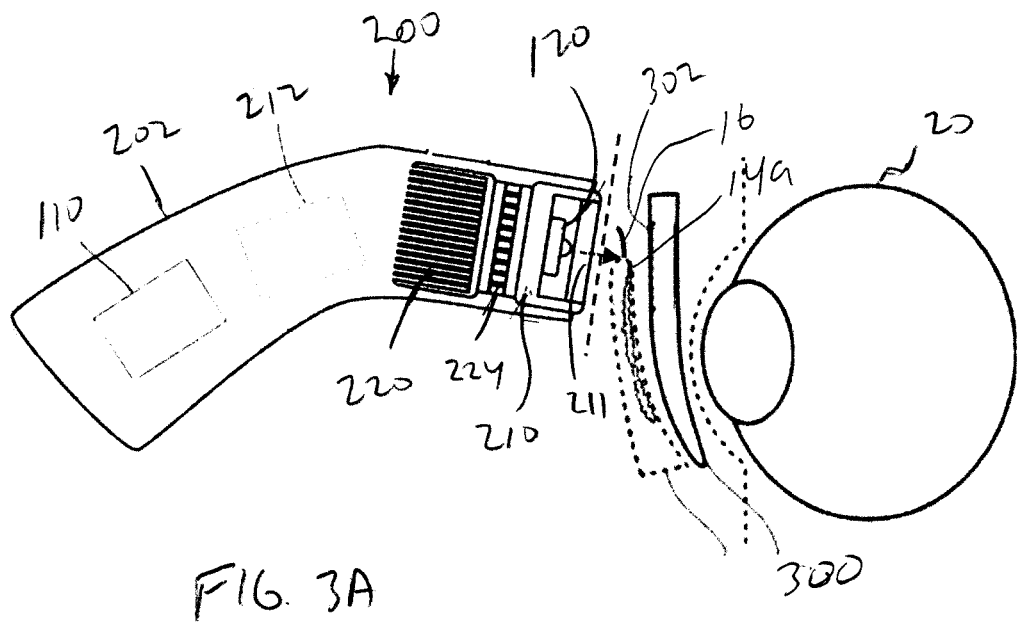
FIG. 3A is a schematic side plan view of another embodiment of an eyelash treatment device having a scleral shield.
Figure 3B:
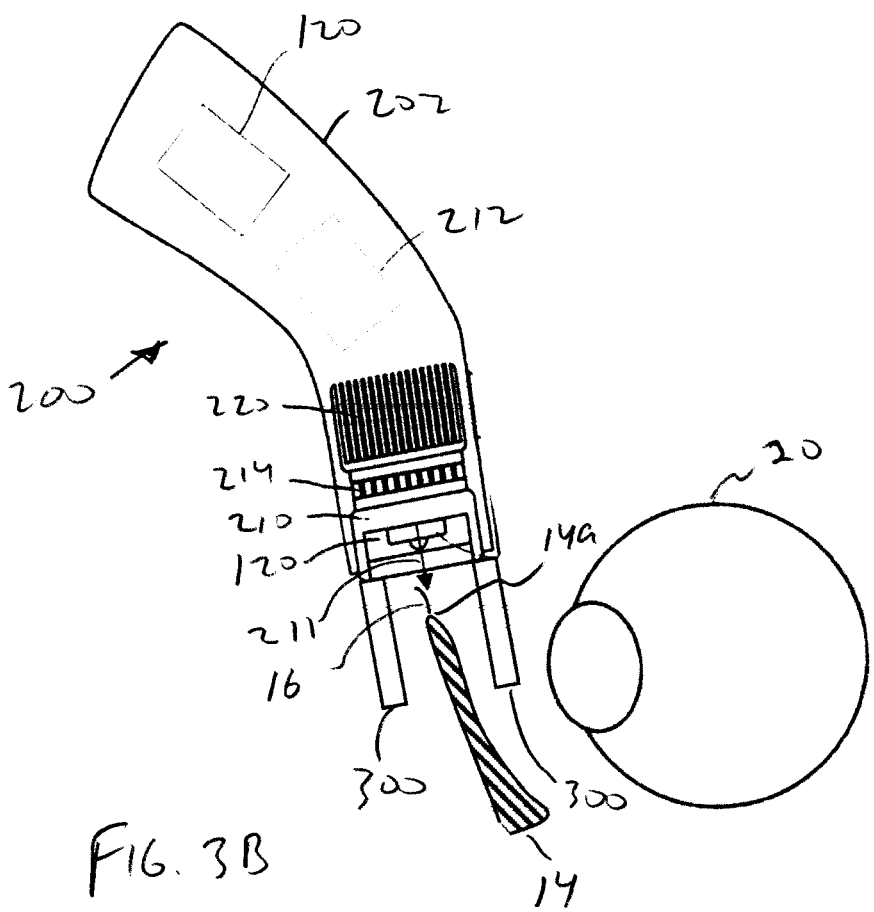
FIG. 3B is a schematic block diagram of an embodiment of an eye diagnostic and treatment device having attached scleral shields.

The eyelash treatment device 200 of FIGS. 3A and 3B may include any or all of the features described in relation to other embodiments presented herein. For example, in the depicted embodiment, the energy transducer module 120 is an infrared LED array. However, in other embodiments, including other embodiments configured to apply energy to one eyelid at a time, the energy transducer module 120 may include an LED emitting light in the visible light spectrum, a laser, an incandescent lamp, a xenon lamp, a halogen lamp, a luminescent lamp, a high-intensity discharge lamp, or a gas discharge lamp. The eyelash treatment device 200 may further include a scleral shield 300 made of light energy blocking material or have a light energy blocking surface on a front face 302 to block light energy from entering the eyeball during treatment. The scleral shield 300 may also incorporate one or more temperature sensors. The eyelash treatment device 200 of FIGS. 3A and 3B may also include a power source module 110 and optionally a controller 212, along with other components as described in relation to various embodiments presented herein. Additionally, the eyelash treatment device 200 includes a reflector 210. In the depicted embodiment, the reflector 210 is formed of a barrel and backplate, which together surround the energy transducer module 120 in all but a distal direction.

In certain embodiments having a controller 212, the controller 212 can receive input instructions from a user (for example, through a user interface device, such as a button, switch, touch screen, voice commands, from another module or device, such as a smartphone) to emit light from the energy transducer module 120. Upon receipt of the user input instructions, the controller 212 can instruct the power source module 110 to deliver energy to or from the energy transducer module 120.

The energy transducer module 120 can be configured to emit light of the appropriate wavelength necessary for the desired treatment. The treatments may include one or more of the following: promoting eyelash growth by the illuminating the eyelid margins, antibacterial treatment to kill bacteria in the eye system 10, and heating the meibomian gland of eyelids 12, 14. Note that the descriptions of the various devices herein (including the eyelash treatment device 200) are exemplary, and not limiting. Thus, for example, while this detailed description mentions particular elements and circuitry having particular functions, this does not limit the disclosure to those particular embodiments. For example, while LEDs are mentioned, other light sources, such as incandescent, xenon, halogen, high-intensity discharge, cold cathode tube, fluorescent, laser and other light sources or energy sources can be used.

For some embodiments, it is desirable to use light with a wavelength selected to: a) stimulate and/or promote eyelash growth at the eyelash region of an eyelid, b) reduce or minimize the amount of light that penetrates beyond the eyelash region, and c) reduce or minimize the amount of heating that occurs at the surface of the eyelid. For example, in some embodiments, the energy transducer 120 can emit light having a wavelength in the range of about 450-700 nm. Furthermore, emitting wavelengths within this portion of the light spectrum avoids the undesired portion of the electromagnetic spectrum for embodiments that do not incorporate a scleral shield, including ultraviolet, infrared, and blue.

In some embodiments, the energy transducer is further configured to provide light energy at a second wavelength selected to treat bacteria. In some embodiments, the energy transducer is further configured to provide light energy at a third wavelength selected to be absorbed by the eyelid tissue, and thereby heat the eyelid tissue. The first wavelength may be in the range of about (without limitation) 450-700 nm, the second wavelength may be in the range of about 400-450 nm and the third wavelength may be in the range of about 700-1000 nm.

While a controller 212 and energy transducer 120 are mentioned, it will be understood that the controller could be integrated with driver circuitry for the light source or circuitry for a solid-state or other power supply, or other configurations could be used to provide the desired result. Further, some or all of the functions described as being handled by, or controlled by, controller 212, may be implemented using discrete logic or analog circuitry, or a combination thereof.

Moreover, although the various embodiments such as device 200 are illustrated schematically, they can be produced in a variety of handheld or stationary configurations with a housing with optional gripping surfaces, manipulation and control structures, and the like.

In one embodiment, a handheld light therapy device 200 includes a housing 202, an energy transducer module 120 positioned at a distal end of the housing, a power source module coupled to the energy transducer module, a controller 212 coupled to the power source module, and a user interface controller coupled to the controller configured to provide user input to the controller to instruct the power source module to deliver energy to or from the energy transducer module. Examples of a user interface include a button, switch, touch screen or voice commands. The user interface may be incorporated into the device, it may be located on another module or device in communication with the handheld light therapy device 200, such as a smartphone that wirelessly communicates with the controller.

The handheld light therapy device 200 further includes a scleral shield 300 configured to block light energy toward the eyeball, the scleral shield being positioned between the energy transducer and the eyeball. In use, the eyelash region is positioned in a gap between the energy transducer and the scleral shield and the energy transducer is instructed to provide light energy 211 at a first wavelength to the eyelash region, and the scleral shield blocks and/or protects the eyeball from the light energy.

It is desirable to use light with a wavelength selected to stimulate and/or promote eyelash growth at the eyelash region of an eyelid. For example, in some embodiments, the energy transducer 120 can emit light having a wavelength in the range of about 450-700 nm. In some embodiments, the energy transducer is further configured to provide light energy at a second wavelength selected to treat bacteria, for example in the range of about 400-450 nm. In some embodiments, the energy transducer is further configured to provide light energy at a third wavelength selected to be absorbed by the eyelid tissue, and thereby heat the eyelid tissue, for example, in the range of about 700-1000 nm.

In some embodiments, the handheld light therapy device 200 may include a display or dashboard configured to display the device status. The display or dashboard may be on the device, such as on the housing, or the display or dashboard may be on a separate device, such as another module or device, or a smartphone in wireless communication. The handheld light therapy device 200 may also use a power cord or a battery configured to power the device components and battery charging means.

The handheld light therapy device 200 may also include a safety feature electrically coupled to the energy transducer prevents or interrupts the light energy from occurring if the scleral shield is not in position to protect the eyeball. In some embodiments, the safety feature may include sensors to make sure that a protective scleral shield 300 is in the correct position prior to turning on an energy transducer module 120, thus preventing damage to the eye system 10, sensors for preventing undesired activation of the device, sensors monitoring the delivery of energy to the patient, or sensors for preventing overheating of the skin. In some embodiments, the safety feature may include safety warning apparatus to let the patient know of an unsafe condition, and can include a flashing light, a flashing warning, a sound warning beep, a picture, a vibration pattern, or words indicative of the potential for or existence of an unsafe condition.

The devices described herein can be designed for use in a plurality of settings, including in-home use and use within an eye care professional's office, a health clinic, or other healthcare facility.

The eyelash treatment device 200 of various embodiments may also include one or more thermal management structures configured to cool at least a portion of the device. In some embodiments, the thermal management structures are provided to manage the heat of the energy transducer module 120 and prevent the device 200 from overheating. Additionally, or alternatively, in some embodiments, the thermal management structures are provided to cool a surface of the eyelid to limit discomfort and avoid injury to the eyelid tissue during treatment. In FIG. 3A, for example, the eyelash treatment device 200 includes a thermal management structure 220 (shown as a finned heat sink), a thermoelectric (Peltier) module 224, and one or more thermally conductive surfaces that are passively or actively cooled. In some embodiments, a passive heat sink may be provided as an adequate thermal management structure 220 to dissipate heat from the energy transducer module 120 into the surrounding environment without the need for a thermoelectric module 224. Some embodiments include a thermoelectric module 224 or other type of cooler (such as a compact vapor-compression cooler) designed to cool the energy transducer module 120 by transferring heat directionally away from the energy transmission surface 140. In FIG. 3A, the thermoelectric module 224 and thermal management structure 220 are coupled such that the thermoelectric module 224 pumps heat away from the energy transducer module 120 towards thermal management structure 220 for dissipation.

The embodiment of FIG. 3B is similar to the embodiment of FIG. 3A except there are two scleral shields 300. The eyelid is placed within the scleral shields 300 during eyelash treatment.

Figure 4:
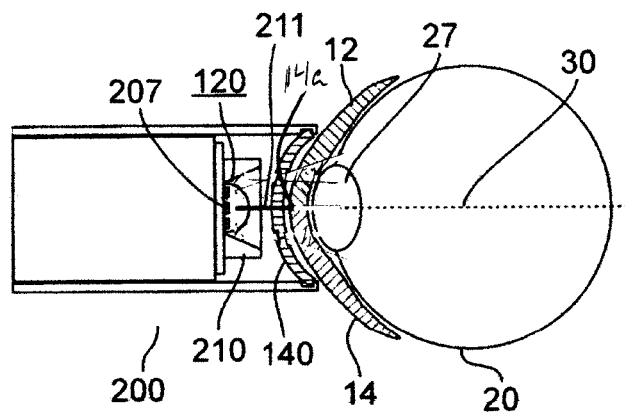
FIG. 4 is a schematic side plan view of another embodiment of an eyelash treatment device.

FIG. 4 is a schematic side plan view of another embodiment of an eyelash treatment device. The eyelash treatment device 200 shown in FIG. 4 is positioned adjacent to an eyeball 20 to stimulate and/or promote eyelash growth at the eyelash region 12a, 14a. For simplicity, sensitive eye structures such as the cornea, iris, pupil lens, and adjacent elements are depicted as a single element called anterior eye structures 27. The eyelash treatment device 200 may include any or all of the features described in relation to other embodiments presented herein, along with additional components useful in operation of the eyelash treatment device 200. The eyelash treatment device 200 can include a power source module 110, a controller 212, an energy transducer module 120, an energy waveguide in the form of reflector 210, and an energy transmission surface 140. Each of these components, either alone, or in combination with other components (either shown herein or not disclosed) can correspond or be part of the modules described in relation to FIGS. 2A-2C and 3A-3B. The components of the eyelash treatment device 200 can be contained in a housing 202. While not shown in the figures, some of the embodiments of the treatment device 200 may also include a consumable portion and/or a scleral shield 300.

The energy transducer module 120 can include a lens 208 that can be used in conjunction with the LED emitter 207 or other electromagnetic energy source to direct the energy to the eyelid at a desired angle or in a desired pattern, at a desired intensity.

The energy transmission surface 140 may be configured to direct energy generated by the energy transducer module 120 toward a desired region. The energy transmission surface 140 may include one or more lenses configured to focus energy generated by the transducer module 120. The energy transmission surface 140 may contact the surface of the eyelid 12, 14. In some embodiments, at least a portion of energy transmission surface 140 may be configured as a single-use cover element.

Figure 5:
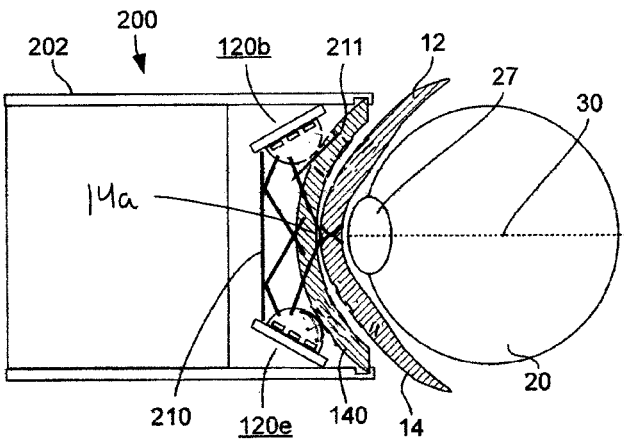
FIG. 5 is a schematic side plan view of another embodiment of an eyelash treatment device, which includes an eyelash treatment device and a scleral shield.

FIG. 5 shows a schematic side plan view of another embodiment of an eyelash treatment device 200. The embodiment of the eyelash treatment device 200 may contain components similar to those shown in FIG. 4, including the power source module 110 and the controller 212, though such components are not shown in FIG. 5. FIG. 5 provides a different configuration for the energy transducer module 120 in order to focus and control the direction of the light beams 211. In some embodiments, the eyelash treatment device 200 can include multiple energy transducer modules 120. Having separate energy transducer modules 120a, 120b positioned separately in the eyelash treatment device 200 reduces the amount of light that may be directed towards sensitive anterior eye structures 27 along the central ocular axis 30.

As depicted in FIG. 5, the upper and lower energy transducer modules 120 can be tilted at an angle, each having a central optical axis directed substantially at an oblique angle to the surface of each eyelid. In some embodiments, the upper and lower energy transducer modules 120 can have other directional orientations. For example, in some embodiments, the upper and lower energy transducer modules 120 can be positioned such that each central optical axis of the illumination sources is substantially horizontal. As such, the light beams 211 transmitted from the energy transducer modules 120 configured in this way can travel horizontally from the energy transducer modules 120 to the energy transmission surface 140 and may then be refracted, diffracted, or reflected at an angle toward the treatment tissue, in a manner that minimizes the proportion of light that reaches the sensitive anterior eye structures 27.

Figure 6:
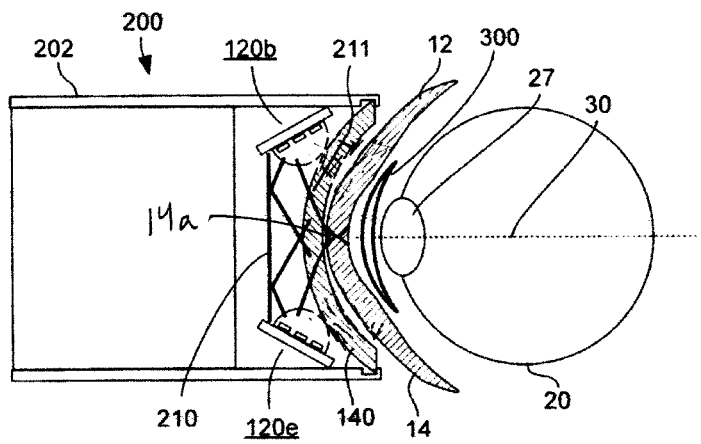
FIG. 6 is a schematic side plan view of another embodiment of an eye treatment system, which includes an eyelash treatment device and a scleral shield.

FIG. 6 is a schematic side plan view of an eyelash treatment device 200, similar to the eyelash treatment device 200 depicted in FIG. 5. Also shown in FIG. 6 is a scleral shield 300, which, in conjunction with the eyelash treatment device 200, can provide a system of treating the target tissue with increased safety and efficacy. The scleral shield 300 can be positioned under eyelids 12, 14 and adjacent to the patient's eyeball 20 to cover sensitive anterior eye structures 27. For example, the scleral shield may be positioned (referring to FIG. 1) over the sclera 21 and cornea 22 and may also provide protection to other internal anatomy of the eye such as the iris 24, pupil 25, lens 25, and other light sensitive anatomy of the eye system 10.

Referring back to FIG. 6, the scleral shield 300 may be of similar disc shape as a contact lens, or it may be substantially larger to cover the entire cornea and optionally at least some of the sclera (as in the case of a conventional corneal shield), or it may have a partial disc or paddle shape, similar to the under-lid portion of a Mastrota paddle. Shield 300 may be positioned in the eye prior to treatment with the eyelash treatment device 200, or it may be integral with device 200, and therefore placed in the eye or under the lid during the treatment. Though the scleral shield 300 is shown in FIG. 6 to be used in the conjunction with the embodiment of the eyelash treatment device 200 described in relation to FIG. 5, it will be appreciated by the skilled artisan that the scleral shield 300 can be used in conjunction with any of the embodiments of the eyelash treatment device 200 disclosed herein to create a system for safe and efficacious treatment of eye disorders.

It will be further appreciated that the scleral shield 300 may include features which provide even more benefits to the device. For example, the scleral shield 300 of some embodiments is configured to reflect energy away from the eyeball and toward the inner eyelids, providing heating to the inner eyelids. In some embodiments, the scleral shield 300 may be made of, or coated with, a light energy blocking material.

In some embodiments, an illumination source emitting blue or violet light in the range of 400-450 nm may be used to reduce and/or eliminate bacteria in the eye system 10. It is known that exposure to visible light, more specifically, blue or violet light wavelengths, causes inactivation of certain bacterial species. Common bacteria include *S. aureus, S. epidermidis, B. oleronius,* and *P. acnes*. In selecting wavelengths in the range of 400-450 nm, a plurality of considerations may be taken into account. For example, it is important that the emitting source (LED) does not emit a significant amount of energy below about 400 nm, which is in the UVA spectrum and can be associated with skin cancer.

In another embodiment utilizing LEDs as an illumination source, the LED emitter 207 can include one or more multi-spectral LEDs or multiple LEDs to emit light of differing or the same wavelength from each LED. In some embodiments, each LED of the LED emitter 207 is configured to emit light of a different wavelength. The LED emitter 207 can emit the light from each differently colored LED either consecutively or simultaneously. For example, in some embodiments, the LED emitter 207 can include a red, green, blue (RGB) LED system, or other multi-spectral LED system, to emit light of various wavelengths in the visible light spectrum and IR spectrum. In some embodiments, the LEDs of the LED emitter 207 can be configured to operate simultaneously to emit white light. Alternatively, in some embodiments, the user can select the wavelength of light to be emitted from the multi-spectral LEDs. Further, an LED with using a special phosphorescent coating may be fabricated in order to produce the most efficient output spectrum relative to input power.

Figure 7:
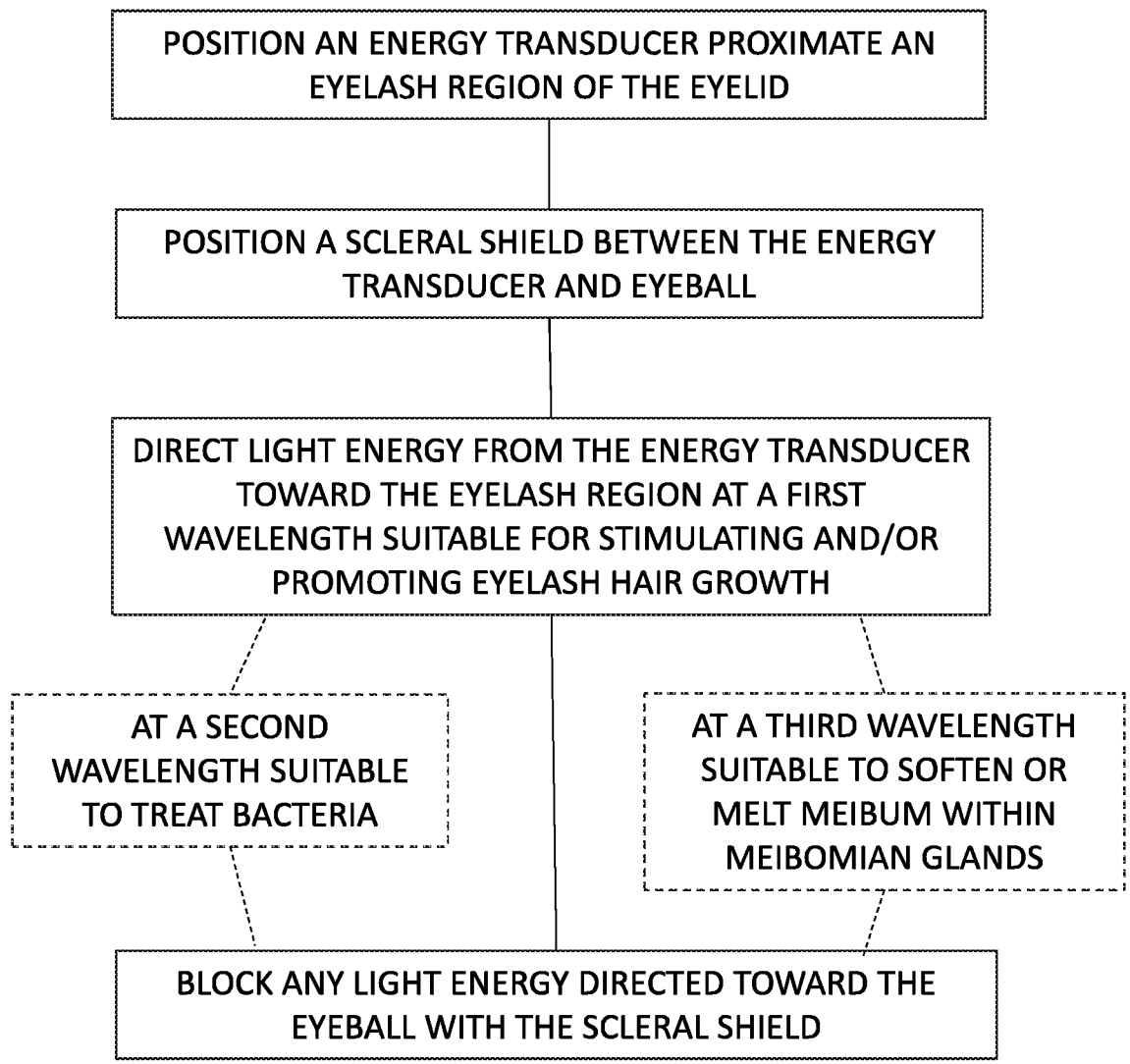
FIG. 7 is a flow chart showing one embodiment of a method for promoting eyelash growth using light energy.

FIG. 7 is a flow chart showing one embodiment of a method for promoting eyelash growth using light energy. The method starts by positioning an energy transducer providing light energy at a first wavelength selected to proximate eyelash growth. For example, a suitable wavelength may be in the range of about 450-700 nm for eyelash growth, but the present invention is not limited to this range. Next a scleral shield is positioned between the energy transducer and eyeball, the scleral shield being made of, or coated with, a light energy blocking material. Light energy is then directed from the energy transducer toward the eyelash region at a first wavelength suitable for stimulating and/or promoting eyelash hair growth. The scleral shield blocks light energy directed toward the eyeball to protect the eyeball from the light energy In some embodiments, the energy transducer may also provide light energy at a second wavelength selected to treat bacteria, for example, a suitable wavelength may be in the range of 400-450 nm. In still other embodiments, the energy transducer may also provide light energy at a third wavelength to soften or melt meibum within meibomian glands, for example, a suitable wavelength may be in the range of about 700-1000 nm. These wavelengths are only examples and the invention is not limited to these ranges.

Patient safety and comfort are important considerations in the present device and method. Safety sensors and warnings can thus advantageously be incorporated into the device. These include sensors to make sure that a protective scleral shield 300 is in the correct position prior to turning on an energy transducer module 120, thus preventing damage to the eye system 10, sensors for preventing undesired activation of the device, sensors monitoring the delivery of energy to the patient, or sensors for preventing overheating of the skin. A safety warning apparatus can be incorporated into the device to let the patient know of an unsafe condition, and can include a flashing light, a flashing warning, a sound warning beep, a picture, a vibration pattern, or words indicative of the potential for or existence of an unsafe condition.

For purposes of summarizing the disclosure, certain aspects, advantages and features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein.

While this disclosure has been described in connection with what are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While the present disclosure has described certain exemplary embodiments, it is to be understood that the disclosure is not limited to the disclosed embodiments, but, on the contrary, is intended to cover various modifications and equivalent arrangements included within the scope of the appended claims, and equivalents thereof.

What is claimed is:

1. A method for promoting eyelash growth, comprising:
    positioning an energy transducer proximate an eyelash region of the eyelid, the energy transducer configured to provide light energy at one or more wavelengths;
    positioning a first scleral shield and a second scleral shield not directly connected to the first scleral shield on respective sides of the eyelash region of the eyelid and the second scleral shield between the energy transducer and eyeball, the first scleral shield and the second scleral shield being made of, or coated with, a light energy blocking material;
    directing light energy from the energy transducer toward the eyelash region at a first wavelength suitable for stimulating and/or promoting eyelash hair growth; and
    interrupting the light energy if the second scleral shield is not in position to protect the eyeball and while the scleral shield is not properly attached to, and aligned with, the energy transducer.

2. The method of claim 1, further comprising directing light energy from the energy transducer toward the eyelid at a second wavelength suitable to treat bacteria.

3. The method of claim 1, further comprising heating the eyelid at a third wavelength suitable to soften or melt meibum within meibomian glands.

4. The method of claim 1, wherein a safety feature electrically coupled to the energy transducer prevents or interrupts the light energy from occurring if one or more of the first scleral shield and the second scleral shield and associated assembly are not properly attached to, and aligned with, the device.

* * * * *